US009052262B2

(12) United States Patent
Van Der Voorn

(10) Patent No.: US 9,052,262 B2
(45) Date of Patent: Jun. 9, 2015

(54) CONTROL OF PARTICLE FLOW IN AN APERTURE

(75) Inventor: Johannes Adrianus Van Der Voorn, Christchurch (NZ)

(73) Assignee: IZON Science Limited, Christchurch (NZ)

( * ) Notice: Subject to any disclaimer, the term of this patent is extended or adjusted under 35 U.S.C. 154(b) by 154 days.

(21) Appl. No.: 13/575,357

(22) PCT Filed: Jan. 26, 2011

(86) PCT No.: PCT/EP2011/051087
§ 371 (c)(1),
(2), (4) Date: Sep. 25, 2012

(87) PCT Pub. No.: WO2011/092218
PCT Pub. Date: Aug. 4, 2011

(65) Prior Publication Data
US 2013/0015066 A1  Jan. 17, 2013

(30) Foreign Application Priority Data
Jan. 27, 2010  (GB) .................................. 1001311.8

(51) Int. Cl.
*G01N 15/12* (2006.01)
*G01N 27/447* (2006.01)

(52) U.S. Cl.
CPC .............. *G01N 15/12* (2013.01); *G01N 27/447* (2013.01)

(58) Field of Classification Search
CPC .............................. G01N 27/447; G01N 15/12
USPC ...................... 422/82.01, 68.1; 204/450–452, 204/600–603
See application file for complete search history.

(56) References Cited

U.S. PATENT DOCUMENTS

| 2,656,508 A | 10/1953 | Coulter |
| 3,015,775 A | 1/1962 | Coulter et al. |

(Continued)

FOREIGN PATENT DOCUMENTS

| EP | 0 608 120 A2 | 7/1994 |
| EP | 1 092 147 | 4/2001 |

(Continued)

OTHER PUBLICATIONS

International Search Report for corresponding International Application No. PCT/EP2011/051087 mailed May 10, 2011.
(Continued)

*Primary Examiner* — Jennifer Dieterle
(74) *Attorney, Agent, or Firm* — Renner, Otto, Boisselle & Sklar, LLP

(57) ABSTRACT

The flow of particles (18) in an aperture (10) between two reservoirs (14) and (15) is controlled by suspending the particles (18) in a fluid (17) within the aperture (10), applying a potential difference across the aperture (10) so as to tend to electrophoretically transport the particles (18) between a region of higher potential field and a region of lower potential in the fluid (17), applying a pressure differential across the aperture (10) so as to tend to transfer the fluid (17) with the particles (18) therein though the aperture (10) from a high-pressure reservoir (14) to a low-pressure reservoir (15), and adjusting the potential difference and/or the pressure differential across the aperture (10) in order to achieve precise control over the translation of the particles (18) within the aperture (10). This permits precise control of velocity and displacement, and the measured delivery of particles in solution through an aperture from one reservoir to another by means of careful command over electrical potential and pressure differential over the aperture.

13 Claims, 7 Drawing Sheets

(56) References Cited

U.S. PATENT DOCUMENTS

| | | | |
|---|---|---|---|
| 3,815,022 A | 6/1974 | Golibersuch | |
| 4,331,862 A | 5/1982 | Ryan | |
| 5,302,264 A | 4/1994 | Welch et al. | |
| 5,429,728 A | 7/1995 | Gordon | |
| 5,578,179 A | 11/1996 | Demorest et al. | |
| 6,004,443 A | 12/1999 | Rhodes et al. | |
| 7,077,939 B1 * | 7/2006 | Crooks et al. | 204/450 |
| 7,279,883 B2 | 10/2007 | Sohn et al. | |
| 7,288,219 B1 | 10/2007 | Roos | |
| 2002/0127144 A1 * | 9/2002 | Mehta | 422/81 |
| 2002/0195344 A1 * | 12/2002 | Neyer et al. | 204/600 |
| 2005/0130317 A1 | 6/2005 | Ventzki et al. | |
| 2006/0154399 A1 * | 7/2006 | Sauer et al. | 438/48 |
| 2006/0163071 A1 * | 7/2006 | Siwy et al. | 205/67 |
| 2009/0111712 A1 * | 4/2009 | Van Den Boom et al. | 506/16 |
| 2009/0205960 A1 * | 8/2009 | Schaffer et al. | 204/452 |

FOREIGN PATENT DOCUMENTS

| | | |
|---|---|---|
| WO | 99/64851 | 12/1999 |
| WO | 2006/063872 A1 | 6/2006 |

OTHER PUBLICATIONS

Form PCT/ISA/237 for corresponding International Application No. PCT/EP2011/051087 dated May 10, 2011.

British Search Report for corresponding UK Application No. GB1001311.8 dated Apr. 21, 2010.

British Search Report for related UK Application No. GB1107712.0 dated Jun. 1, 2011.

DuBlois and Wesley, "Sizes and Concentrations of Several Type C Oncornaviruses and Bacteriophage T2 by the Resistive-Pulse Technique", Journal of Virology, Aug. 1977, p. 227-233 (cited on p. 1, line 15 of the specification).

British Examination Report for corresponding UK Application No. GB1001311.8 dated May 19, 2011.

British Examination Report for corresponding UK Application No. GB1001311.8 dated Jan. 6, 2011.

* cited by examiner

CONTROL OF PARTICLE FLOW IN AN APERTURE

BACKGROUND OF THE INVENTION

This invention relates generally to particle sensitive or radiation sensitive systems for detecting, measuring or controlling particles and/or radiation, and is concerned with the manipulation of particle flow though a small aperture in order to accomplish accurate measurement of particle flow for example, and/or detailed control of reactions, translocation and aggregation of materials.

The ability to control the transport of nano-scaled particles and to determine the characteristics of such particles has utility in the fields of molecular biology, biochemistry, biotechnology, genetics, medicine and nano-scale technologies.

DuBlois and Wesley, in "Sizes and Concentrations of Several Type C Oncornaviruses and Bacteriophage T2 by the Resistive-Pulse Technique", JOURNAL OF VIROLOGY, August 1977, p. 227-233, describe a Nanopar counter, that is a Coulter counter adapted to measure nanoscale particles. This counter has the ability to electrophoretically measure the quantity of particles of a certain size that travel though an aperture under the effect of voltage and pressure differentials across the aperture. However, the described device lacks the ability to selectively change the voltage and pressure over the aperture in order to control the velocity and displacement of particles and therefore increase the sensitivity of the instrument or allow for individual particle displacement control.

U.S. Pat. No. 6,004,443 teaches a method for controlling sample dispersion in a separation column during free-fluid electrophoresis in a capillary by detecting sample dispersion and correcting the dispersion by instituting an imbalance between pressure induced flow and electroosmotic flow. This improved method of capillary electrophoresis allows for the exact control of particles in capillary, which has advantage in that medium will be optimally separated in the capillary. However the separation of particles is not from one reservoir to another, and furthermore there is no proposal to diffuse particles from one reservoir to another. Also, the control of particles for aggregation or reaction in one reservoir is not achieved by this method.

U.S. Pat. No. 7,279,883 discloses an innovative miniature Coulter counter that is manufactured utilizing microfabrication techniques. The counter incorporates a micro- or nanofluidic system to force particles though the conduits of the device so that the impedance of the device will alter according to the nature of the particles and enable the measurement of the particles. The manufacturing technique allows for multiple size conduits to be employed simultaneously on a sample, thereby allowing for the detection of many different particles in one solution. However the device does not allow for the exact control of induced or electroosmotic flow of particles, and is therefore limited in its application to the detection of particles.

U.S. Pat. No. 7,077,939 discloses a method for particle control and detection utilizing the combination of electrophoresis and pressure over a single nanotube embedded in a membrane. However the method does not allow for the real time adjustment of both pressure and current in order to exactly control the velocity and displacement of particles. Also, the use of carbon nanotubes as apertures for the electrical detection of particles influences the measurement. A carbon nanotube by nature has high electrical conductivity and as such dominates the electrical properties of the aperture that it forms. Therefore the small change in the electrical properties of the aperture when a particle travels though it are masked by the presence of the carbon nanotube.

U.S. Pat. No. 4,331,862 teaches a method for calibrating blood particle counters utilizing particles of different sizes and concentrations at different flow rates. However the calibration method does not include control of the variables of electrical potential and aperture size. The method is therefore limited in its application to processes where flow rate, particle size and particle concentration are the only variables that can be altered.

PCT/EP2005/053366 discloses an adjustable elastomeric aperture that can be adjusted for the purpose of detecting, measuring and controlling particles and/or electromagnetic radiation. The disclosed device is most typically fabricated by penetration of sheets of elastomeric material pre-cut into cruciform geometries.

It is an object of the invention to overcome disadvantages of prior systems by combining electrical potential and pressure differential across an aperture in order to create precise control of nano-scale particle movement in micro- and nano-fluidic applications.

SUMMARY OF THE INVENTION

According to one aspect of the present invention there is provided a method of controlling the flow of particles in an aperture between two reservoirs, the method comprising suspending the particles in a fluid within the aperture, applying a potential difference across the aperture so as to tend to electrophoretically transport the particles between a region of higher potential and a region of lower potential in the fluid, applying a pressure differential across the aperture so as to tend to transfer the fluid with the particles therein through the aperture from a high-pressure reservoir to a low-pressure reservoir, monitoring particles before and/or during and/or after passage through the aperture, and adjusting the potential difference and/or the pressure differential across the aperture in order to achieve precise control over the translation of the particles within the aperture. Electrophoresis is a known technique for achieving suspended particle flow from a higher potential field to a lower potential in a fluid medium. However the invention combines such a technique with the application of a pressure differential to effect fluid transfer from the high-pressure reservoir to a low-pressure reservoir though the aperture, in order to achieve precise control over the translation of particles. The invention exploits the ability of modern electronics to apply accurate measurements and precise control over the pressure differential and the electrical potential, as well as the exact determination of electrical current flow to measure, control and manipulate the movements of particles through the aperture. It is possible to control and measure the number of particles flowing though the aperture by varying the pressure differential and the electrical potential in order to deliver exact amounts of particles to a reaction and to separate particles in solution.

In a preferred embodiment of the invention the potential difference and/or the pressure differential across the aperture is adjusted during translation of the particles through the aperture to control the velocity of the particles, so that accurate measurements of the particle size, velocity, particle charge, Zeta-potential and/or concentration can be made.

In one embodiment of the invention the potential difference and/or the pressure differential across the aperture is adjusted to control the delivery through the aperture of an exact required quantity of particles to one of the reservoirs. This enables particle flow control in such a manner that the particles can be translated from one reservoir to another in a controlled fashion. Such a control technique can be used to deliver the exact required amount of particles to a reservoir, as well as to control diffusion of the particles though a fluid medium and aggregation of the particles in a reservoir.

In one embodiment of the invention the velocity, charge and/or Zeta-potential of the particles is determined in dependence on the potential difference and/or the pressure differential applied across the aperture.

In one embodiment of the invention the particle size of the particles is determined in dependence on the potential difference and/or the pressure differential applied across the aperture.

In one embodiment of the invention the concentration of the particles in the fluid is determined in dependence on the potential difference and/or the pressure differential applied across the aperture.

In one embodiment of the invention the concentration of the particles in the fluid is determined by monitoring the quantity of particles that pass through the aperture in a particular time period.

In one embodiment of the invention the concentration of the particles in the fluid is determined by monitoring (i) the quantity of particles that pass through the aperture under different pressure conditions, and (ii) the quantity of particles in a fluid of known particle concentration that pass through the aperture under different pressure conditions.

In one embodiment of the invention the particles in the fluid are pre-calibrated, and the size of the aperture is determined according to the effect of the potential difference and/or the pressure differential applied across the aperture on the pre-calibrated particles.

In one embodiment of the invention the particles in the fluid are of different types, and the identity of at least one type of the particles is determined according to the effect of the potential difference and/or the pressure differential applied across the aperture as the particles flow through the aperture. This enables different particles to be identified as they flow through the aperture.

In one embodiment of the invention the particles in the fluid are of different charges, and the particles of different charges are separated from one another in dependence on the different effects of the potential difference and/or the pressure differential applied across the aperture on the particles.

In one embodiment of the invention a potential difference of a first polarity is applied across the aperture so as to tend to electrophoretically transport the particles in one direction in the fluid and a potential difference of a second polarity is applied across the aperture so as to tend to electrophoretically transport the particles in a direction opposite to said one direction in the fluid, and such application of potential differences of said first and second polarities is varied so as to tend to control and/or monitor translocation of particles through the aperture.

In one embodiment of the invention the particles are monitored by a monitoring probe which provides an output indicative of the position of at least one of the particles with respect to time, the monitoring probe preferably utilizing one of fluorescence microscopy, nanoparticle tracking analysis, other microscopy based imaging, phase analysis light scattering and near Infrared chemical imaging.

In one embodiment of the invention the degree of aggregation of the particles is determined in dependence on the potential difference and/or the pressure differential applied across the aperture.

In one embodiment of the invention a predetermined quantity of particles is delivered to a reaction in dependence on the potential difference and/or pressure differential applied across the aperture.

In one embodiment of the invention the particles are monitored by a monitoring probe that provides an output indicative of the particles detected, the monitoring probe preferably utilizing one of fluorescence spectroscopy, mass spectroscopy, X-ray spectroscopy, atomic absorption spectroscopy, infrared spectroscopy, near infrared spectroscopy, Raman spectroscopy, static laser scattering, dynamic light scattering, phase analysis light scattering, nanoparticle tracking analysis and surface plasmon resonance.

In one embodiment of the invention the viscosity of the fluid is varied whilst the particles are monitored.

Furthermore the invention may be arranged to establish the combination of aperture size and pressure differential across the aperture that will result in the delivery of a precise amount of volume flow for micro- and nano-fluidic applications.

According to another aspect of the present invention there is provided an electrophoresis system for controlling the flow of particles in an aperture, the system comprising a high-pressure reservoir, a low-pressure reservoir, a wall extending therebetween and defining the aperture extending from the high-pressure reservoir to the low-pressure reservoir, electrode means for applying a potential difference across the aperture so as to tend to electrophoretically transport particles suspended in a fluid within the aperture between a region of higher potential field and a region of lower potential, pressurising means for applying a pressure differential across the aperture so as to tend to transfer the fluid with the particles therein through the aperture from the high-pressure reservoir to the low-pressure reservoir, and adjustment means for adjusting the potential difference and/or the pressure differential across the aperture in order to achieve precise control over the translation of the particles within the aperture.

According to another aspect of the present invention there is provided a method of controlling the flow of particles in an aperture, the method comprising suspending the particles in a fluid within the aperture, applying a potential difference across the aperture so as to tend to electrophoretically transport the particles between a region of higher potential and a region of lower potential in the fluid, and adjusting the temperature of the fluid in the aperture in order to achieve precise control over the translation of the particles within the aperture.

According to another aspect of the present invention there is provided a method of controlling the flow of particles in an aperture, the method comprising suspending the particles in a fluid within the aperture, applying a potential difference across the aperture so as to tend to electrophoretically transport the particles between a region of higher potential and a region of lower potential in the fluid to produce an output current, and adjusting the current in order to achieve precise control over the translation of the particles within the aperture.

BRIEF DESCRIPTION OF THE DRAWINGS

In order that the invention may be more fully understood, reference will now be made, by way of example, to the accompanying drawings, in which.

DETAILED DESCRIPTION OF THE DRAWINGS

Figure 1:
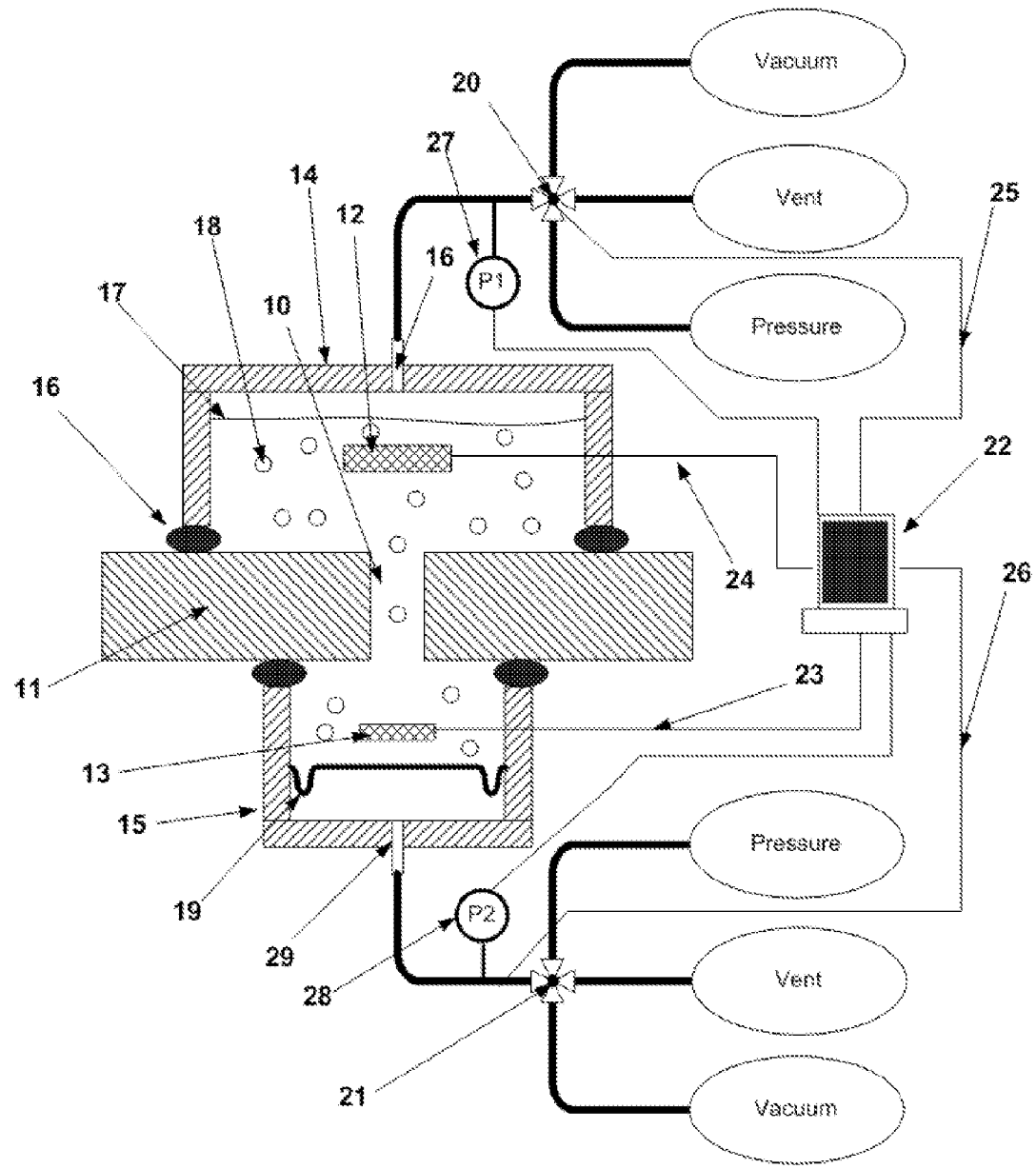
FIG. 1 diagrammatically illustrates an electrophoresis system in accordance with one embodiment of the invention.

FIG. 1 diagrammatically illustrates an electrophoresis system constituting one possible embodiment of the invention. The system includes a substrate wall 11 defining an aperture 10 extending between an upper high-pressure reservoir 14 and a lower low-pressure reservoir 15 and containing a fluid 17. Seals 16 are provided between the upper reservoir 14 and the substrate wall 11 and between the substrate wall 11 and the lower reservoir 15 to ensure that the fluid 17 does not escape from the reservoirs 14 and 15. In addition to the fluid 17, the upper reservoir 14 contains particles 18 suspended in solution, as well as an upper electrode 12 and an upper pressure port 16. The lower reservoir 15 contains particles 18 suspended in solution, a lower electrode 13, a lower pressure port 29 and a diaphragm 19. The diaphragm 19 is not required but is a preferred embodiment to separate the fluid 17 from gas in the vicinity of the pressure port 29. Other methods of fluid-gas separation are known to those skilled in the art and can be used in place of such an arrangement.

The material of the substrate may include, but is not limited to, metals such as titanium, copper, silicon, aluminium, steel or a combination thereof; polymers such as polyethylene, polypropylene, polyurethane, rubber, thermoplastics or a combination thereof; and may include all aforementioned materials with appropriate coatings added for desired surface properties, as will be known per se. The aperture 10 can be fabricated by a number of methods that will be known to those skilled in the art to be applicable to the substrate material. These fabrication methods include, but are not limited to ablation, melting, etching, punching, drilling, probing, casting, chemical vapour deposition, spin casting and the like.

The upper pressure port 16 is connected via tubing to an upper pressure regulator 20 that controls the pressure within the upper reservoir 14. The pressure supply to the regulator 20 can be from a vacuum reservoir, to atmosphere or to a pressurized tank, or to a combination of these, so that the regulator 20 can adjust the pressure in the upper reservoir 14 to any desired level. A pressure gauge 27 monitors the pressure in the upper reservoir 14. The regulator 20 can be set to deliver any pressure that the user desires within the lower limit of the vacuum reservoir to the upper limit of the pressure tank.

In one embodiment of the invention, the regulator 20 is a mechanical regulator that can be manually set to either a certain vacuum, or a certain pressure, or can be left open to the vent. The regulator 20 will then control the pressure in the upper reservoir 14 to this set pressure within the error bounds of the regulator 20, as known to those skilled in the art.

In another embodiment of the invention, the regulator 20 is electronic and is controlled via a communication line 25 by a software program within a computer 22. In this embodiment, the user can choose or set the pressure in the upper reservoir 14. The computer 22 can generate a control signal based on the difference between this set pressure and the measurement of the pressure gauge 27, as will be obvious to those skilled in the art. This control signal can be sent to the regulator 20 via the communication line 25 and the regulator 20 adjusts accordingly in order to alter the pressure in the upper reservoir 14 to the desired pressure.

The lower pressure port 29 is connected via tubing to a lower pressure regulator 21 in similar fashion to the connection of the upper pressure port 16 to the upper pressure regulator 20. As in the case of the upper reservoir pressure control, the lower pressure regulator 21 can be either manually set to a desired pressure or electronically controlled via a communication line 26 from the computer 22. The regulator 21 can be also be connected to a certain vacuum, to a certain pressure, or vented to the atmosphere. The pressure in the lower reservoir 15 is monitored by a pressure gauge 28.

In one implementation of the invention, the electrical potential of the electrode 12 is controlled by the computer 22 via a communication line 24. In another implementation of the invention, the electrical potential of the electrode 12 is manually controlled.

Regardless of the implementation, the amount of current flowing to the electrode 12 though the communication line 24 is monitored and recorded by the computer 24.

In a similar fashion, the electrical potential of the electrode 13 is either manually set, controlled by the computer 22 via a communication line 23, or connected to ground. In one implementation of the invention, the computer 22 monitors and records the current in the communication line 23.

As described in WO 2006/063872 A1, when an electrical potential difference is applied across the electrodes 12 and 13, there will be a current flow between the electrodes 12 and 13. The same current will flow though the communication lines 23 and 24. As will be apparent to those skilled in the art and as further described in WO 2006/063872 A1, when the particles 18 pass through the aperture 10, the electrical characteristics of the aperture 10 will be altered and this will alter the current flow between the electrodes 12 and 13 and thus through the communication lines 23 and 24. This change in the current is referred to as an event and is dependent on a number of variables as described in WO 2006/063872 A1, including the size of the aperture 10, the potential difference across the electrodes 12 and 13, the size of the particles 18 and the velocity of the particles 18 through the aperture 10.

Figure 2:
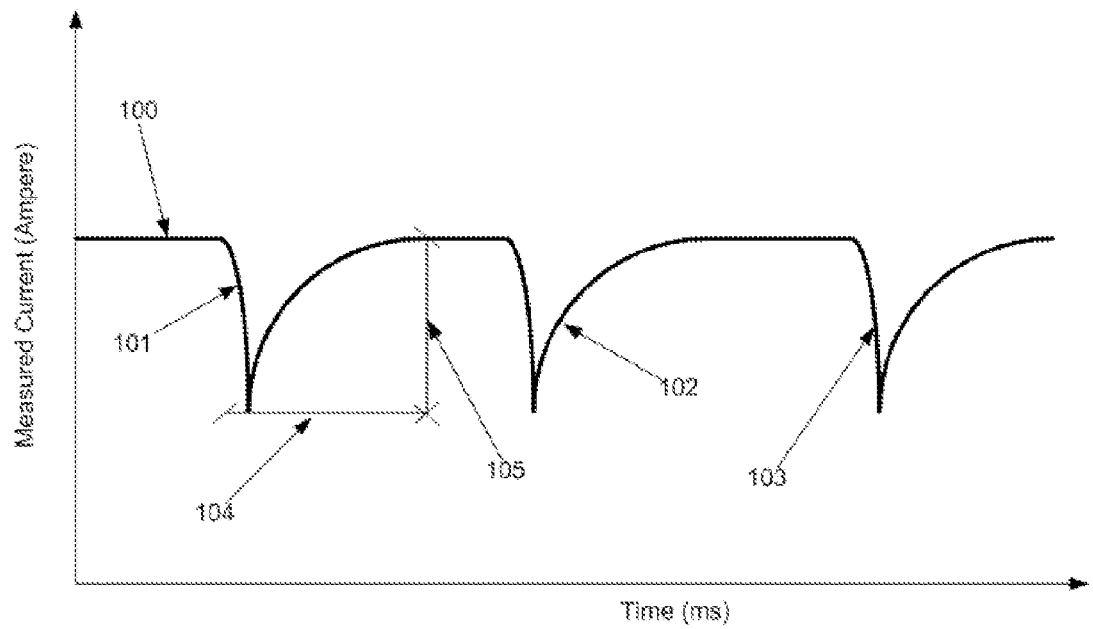
FIG. 2 is a graph of current against time, showing traces of representative measurements obtained in use of such an electrophoresis system.

The graph of FIG. 2 shows a typical current versus time profile 100 as the particles pass though the aperture for a given set of variables as described above. If all the variables remain constant, the current traces during events 101, 102 and 103 as the particles pass through the aperture 10 will be identical in shape, duration 104 and amplitude 105. However altering some of the variables described above will change the shape of the trace during an event. For instance, and as will be apparent to one skilled in the art, if the potential difference across the electrodes 12 and 13 is altered, the amplitude 105 of the trace will either increase or decrease.

In one embodiment of the invention, the particles 18 are moved though the aperture 10 by means of electrophoresis by applying a potential difference across the electrodes 12 and 13 as described above. The direction of the resulting movement of the particles 18 will be dependent on the polarity of the potential difference between the electrodes 12 and 13.

In another embodiment of the invention, the fluid 17 is forced through the aperture 10 by applying a pressure differential between the upper reservoir 14 and the lower reservoir 15 by the means described above. The direction of the flow of the fluid 17 through the aperture 10 will be in the direction from the upper reservoir 14 with higher relative pressure to the lower reservoir 15 with lower relative pressure. When the fluid 17 flows through the aperture 10, it will transport particles 18 through the aperture 10 in the direction of the fluid flow.

In another embodiment of the invention the transport of the particles 18 by means of the application of pressure is used to calculate the concentration of particles.

In one embodiment of the invention, the flow of the particles 18 through the aperture 10 is controlled by a combination of the pressure differential across the reservoirs 14 and 15 and the potential difference across the electrodes 12 and 13.

In one embodiment of the invention, the velocity of the particles 18 passing through the aperture 10 is controlled by a controlling pressure differential across the reservoirs 14 and 15 and the potential difference across the electrodes 12 and 13.

Furthermore, in one embodiment of the invention, the translation of the particles 18 is exactly controlled through the aperture 10 by controlling the pressure differential across the reservoirs 14 and 15 and the potential difference across the electrodes 12 and 13.

As will be apparent to those skilled in the art, for a given data-capturing device, the accuracy of capture is determined by the quantity of data points recorded for a given event. In one embodiment of the invention, the data-capturing device will record 100,000 data points per second or at a rate of 100 kHz. Thus, if a particle 18 travels through the aperture 10 in 0.001 seconds, the data capturing device will record 1,000 points of said event. If the velocity of the particle 18 is decreased such that it passes through the aperture 10 in 0.01 seconds, the same data capturing device will record 10,000 points of said event, thereby increasing the accuracy of the recording.

As will be apparent to those skilled in the art, higher accuracy measurements can be taken by increasing the amplitude of the measurement with respect to the limits of the data capturing device. An analog to digital (A/D) converter is a ubiquitous device that translates electrical potential or current from an analog signal to a digital signal so that it can be recorded by a computer. A/D's have typical analog input ranges of 0-5V, 0-10V, −5-5V, −10-10V, 0-5 mA, 0-10 mA and so forth. This input range represents the conversion accuracy of the device. For instance, a typical 16-bit A/D has a range of 65,536 bits to which it converts the input signal. Accordingly, for an input range of 0-5V, a 16-bit device will be able to record in increments of 5/65,536 or 76.3 microvolt per bit. Thus, if the amplitude of the input signal is 0.25V for instance, the A/D will deliver 0.25/0.0000763 or 3,276 bits to the recording device. In order to make higher accuracy measurements of the 0.25 amplitude signal, a common practice in the art of signal conditioning is to amplify the signal. For instance, if the 0.25V analog signal is amplified to 2.5V, the A/D will deliver 32,765 bits to the recording device, thereby increasing the accuracy of the measurement ten fold.

Figure 3:
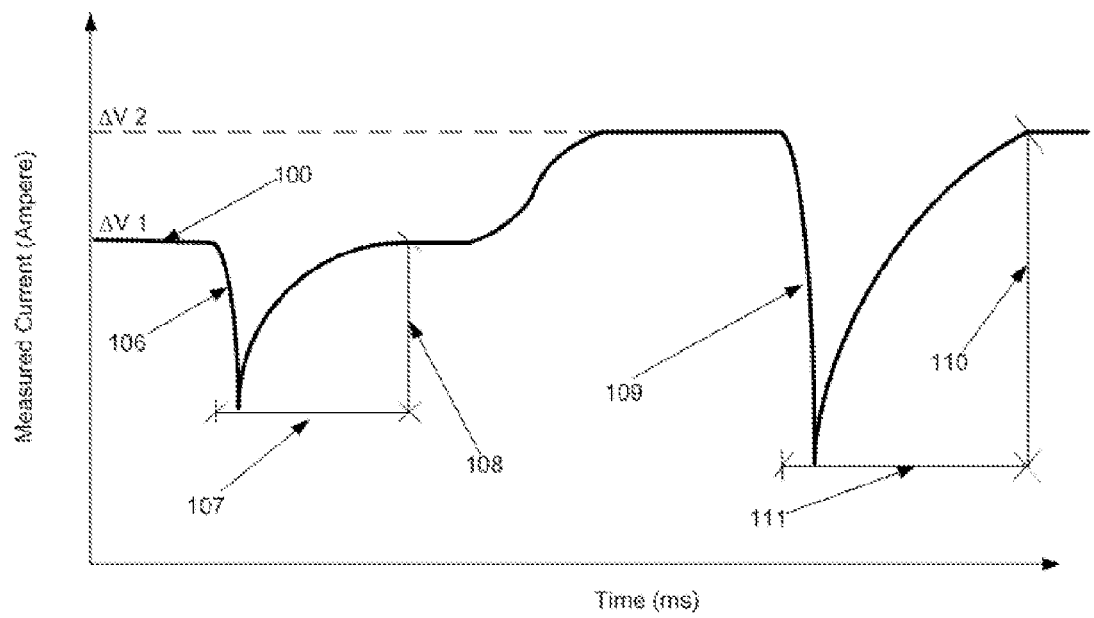
FIG. 3 is a graph of current against time, illustrating the ability of the system to zoom in on current versus time measurements.

FIG. 3 illustrates the possible effect that the combination of increasing the electrical potential across the electrodes 12 and 13 and altering the pressure differential to slow the flow of a particle will have on a current versus time trace 100. When two similar particles 18 are forced through the aperture 10 at different velocities and different electric potentials, the particle with lower electrical potential ($\Delta V1$) and higher velocity will create an event trace 106 with an amplitude 108 and a duration 107 when passing through the aperture 10. An identical particle 18 that is forced though the aperture 10 at lower velocity and with higher electrical potential ($\Delta V2$) will create an event trace 109 with an amplitude 110 significantly higher than the amplitude 108 and a duration 111 significantly longer than the duration 107. This enables an increase in the accuracy of measurement of the particle 18 when passing through the aperture 10 firstly by capturing more data points for a given event and secondly by amplifying the signal as discussed in this paragraph.

It will accordingly be appreciated that an important optional feature of the invention provides a user with the ability to alter the pressure differential and the electrical potential difference across an aperture, so as to increase the accuracy of measurement of a particle passing through the aperture 10.

It will also be appreciated that an important optional feature of the invention provides a user with the ability to physically zoom in on a specific measurement.

It will also be appreciated that an important optional feature of the invention provides the user with the ability to measure small physical changes in similar particles based on small differences in event traces. Since the system is able to capture highly accurate traces, the user will be able to distinguish between small differences in similar particles.

It will also be appreciated that an important optional feature of the invention provides the user with the ability to distinguish between particles of different sizes and charge. The accuracy of the measurement of the device will allow the user to distinguish between traces of different particles.

It will also be appreciated that an important optional feature of the invention provides the user with the ability to correlate event traces under certain potential and pressure gradients with the same size aperture 10. When the controllable parameters of the system are kept constant, the event trace 100 can be calibrated to specific particles and thus facilitate particle signature definition.

Another important optional feature of the invention provides the user with the ability to characterize the hole size of the aperture 10. Referring to FIG. 3, when the same particles 18 in the same concentrations are forced through an aperture 10 with a constant pressure and electrical potential gradient, the only parameter that can change the amplitude 109 and the duration 108 of the event trace 106 is the size of the aperture 10. Thus it is possible to calibrate the specific amplitude and duration of an event for a specific particle and the specific particle concentration in a specific solution, as well as a specific pressure gradient and specific electrical potential gradient to a specific aperture hole size.

Figure 4:
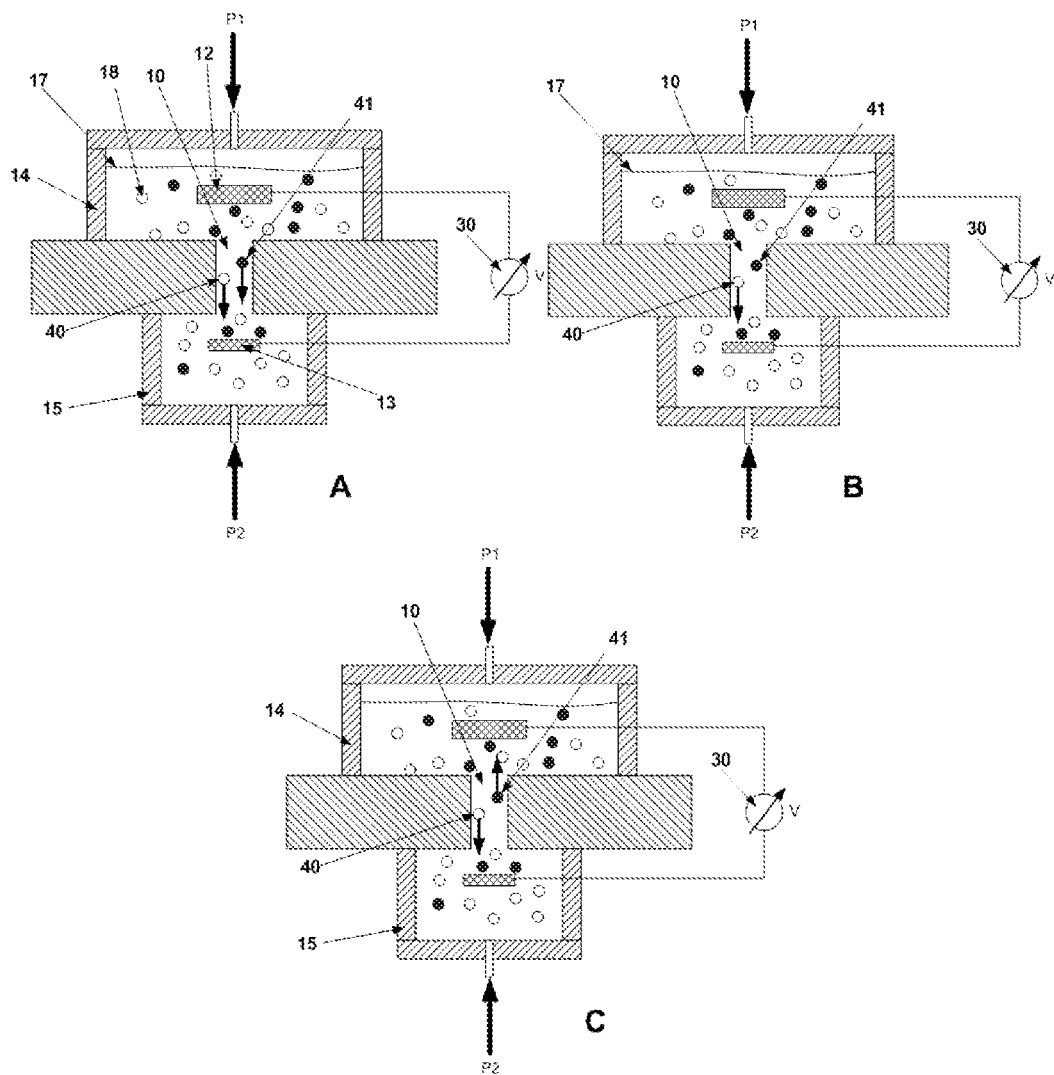
FIG. 4 diagrammatically illustrates three phases A, B and C in use of an electrophoresis system in one possible application of the invention showing the principle of particle flow manipulation and separation.

Another important optional feature of the invention provides the user with the ability to separate particles with different charges. Referring to FIG. 4, the particles 40 and 41 are of the two different types of particles with different charges suspended in the fluid 17. The pressure P1 applied to the upper reservoir 14 is higher than the pressure P2 applied to the lower reservoir 15, and as a result the fluid 17 is forced from the upper reservoir 14 through the aperture 10 into the lower reservoir 15. This flow is a function of the difference in pressure between the reservoirs (P1-P2). As fluid 17 flows through the aperture 10, it transports with it the particles 40 and 41 in suspension (FIG. 4A). As described above, applying an electrical potential 30 across the electrodes 12 and 13 will increase or decrease the flow of particles through the aperture 10 according to the charge of the particles. Therefore, there exists an electrical potential 30 such that one particle 40 of a specific charge will pass through the aperture 10 due to the fluid 17 flow while another particle 41 of another specific charge will remain stationary due to electrophoresis (FIG. 4B). There also exists a charge 30 for which one particle 40 of certain charge will flow through the aperture 10 in one direction and another particle 41 of a different charge will flow through the aperture 10 in another direction (FIG. 4C). When particles 40 and 41 of different charges flow in different directions through the aperture 10, they will be separated out in solution.

If the pressure differential is chosen to be zero, the charge and Zeta-potential of the particles can be extracted from the pertinent pulse durations, as will be apparent to those skilled in the art. The calculation is only straightforward if electrophoresis is dominant, and hence transport time can be linked directly to electrophoretic mobility. Varying the pressure so as to equalise the driving force through electrophoresis and practically stopping particles from translocation through the aperture is another possible way of extracting the particle charge.

Figure 5:
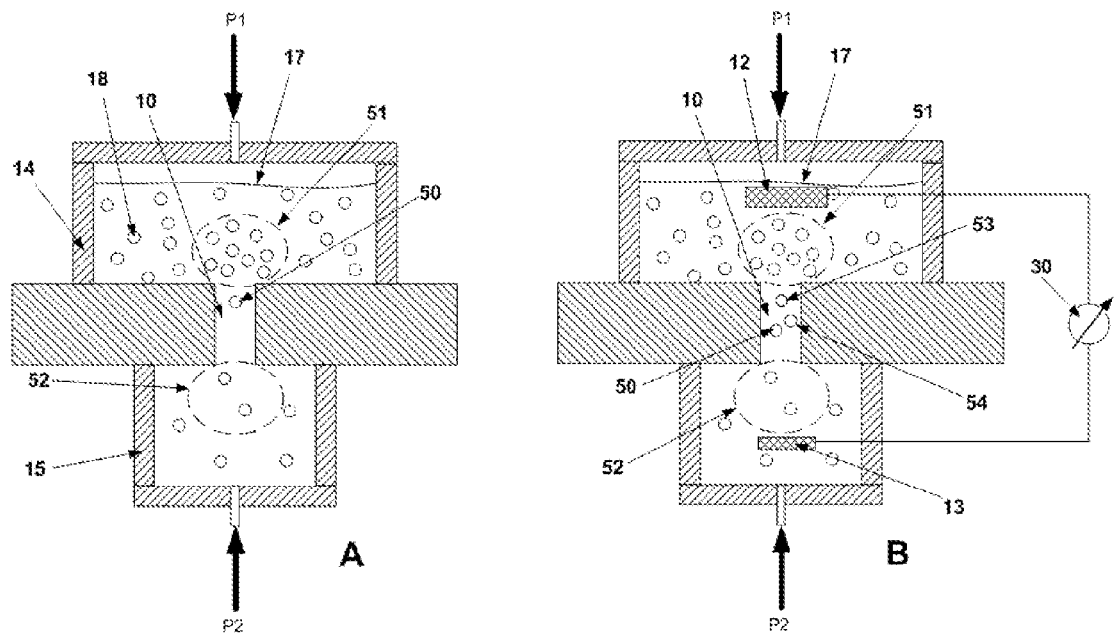
FIG. 5 diagrammatically illustrates two phases A and B in use of an electrophoresis system in another possible application of the invention showing how the system can be used to control translocation through the aperture.

Another application of the invention is to control translocation of particles from one reservoir to another. FIG. 5 illustrates the system in operation where there is a difference in the concentration of the particles 18 in the fluid 17 between the reservoirs 14 and 15. In FIG. 5A, the pressure differential P1-P2 is zero, and natural diffusion will cause particle 50 to travel from a region 52 of higher particle concentration to a region 51 of lower particle concentration through the aperture 10. In FIG. 5B, the pressure differential P1-P2 is positive such that the fluid 17 is forced through the aperture 10. The fluid 17, travelling from the region 51 of higher concentration to the region of low concentration 52, brings with it particles 50, 53 and 54, thus increasing the rate of translocation of particles between the regions. Referring to FIG. 5B, the rate of diffusion can be further increased by applying an appropriate potential 30 over electrodes 12 and 13 such that it will enhance the velocity of the particles 50, 53 and 54 through the aperture 10, increasing the rate of translocation even further. Conversely, when the polarity of the potential 30 across the electrodes 12 and 13 is reversed, the net effect will be to slow down the velocity of the particles travelling through the aperture 10, thereby slowing down the rate of particle translocation between the regions 51 and 52. Furthermore, if the pressure differential P1-P2 is negative, the fluid 17 will flow from the region 52 to region 51 and can cause reverse particle translocation, depending on the potential 30 across the electrodes 12 and 13. As will be apparent to those skilled in the art, careful control of the combination of the pressure differential P1-P2 and the potential 30 across the electrodes 12 and 13 enables the user to control the rate of translocation of particles between the regions 51 and 52 of higher and lower concentration.

Diffusion can be monitored/quantified by reversing the voltage and measuring event frequencies. If the particles are small and fast they will diffuse away from the area of the aperture faster than larger particles, and hence the event frequencies at reverse voltage vary in proportion with the diffusion constant and the particle size.

Figure 6:
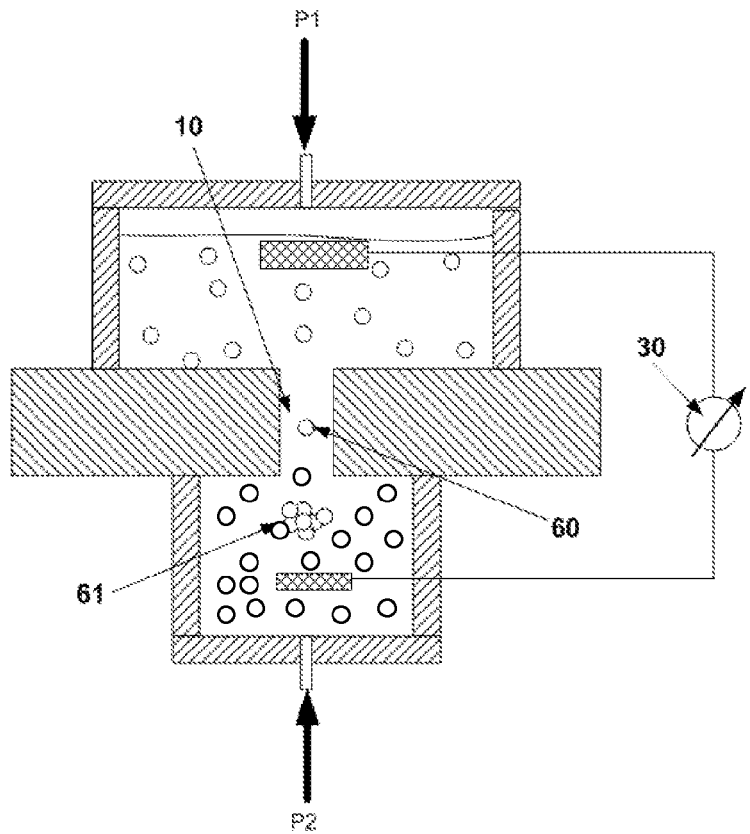
FIG. 6 diagrammatically illustrates the use of an electrophoresis system in another possible application of the invention showing the ability of the system to manipulate aggregation.

Another application of the invention is to enable the user to control aggregation of the particles. As described above, the invention has the ability to carefully control and measure the translocation of the particles through the aperture 10. Referring to FIG. 6, if particles 60 tend to aggregate 61 when they come into contact with one another, the invention will enable the user to carefully control the quantity of particles 60 that are available for aggregation and will thus enable control of aggregation 61. The aggregates can be analysed by reversing the voltage and driving the aggregates through the aperture 10 from the bottom reservoir to the top reservoir. It should be noted that the particles in the top reservoir need not be the same as the particles in the bottom reservoir. If particles in the top and bottom reservoirs are not the same, mixed aggregates can form when particles 60 are translocated from the top reservoir to the bottom reservoir.

Figure 7:
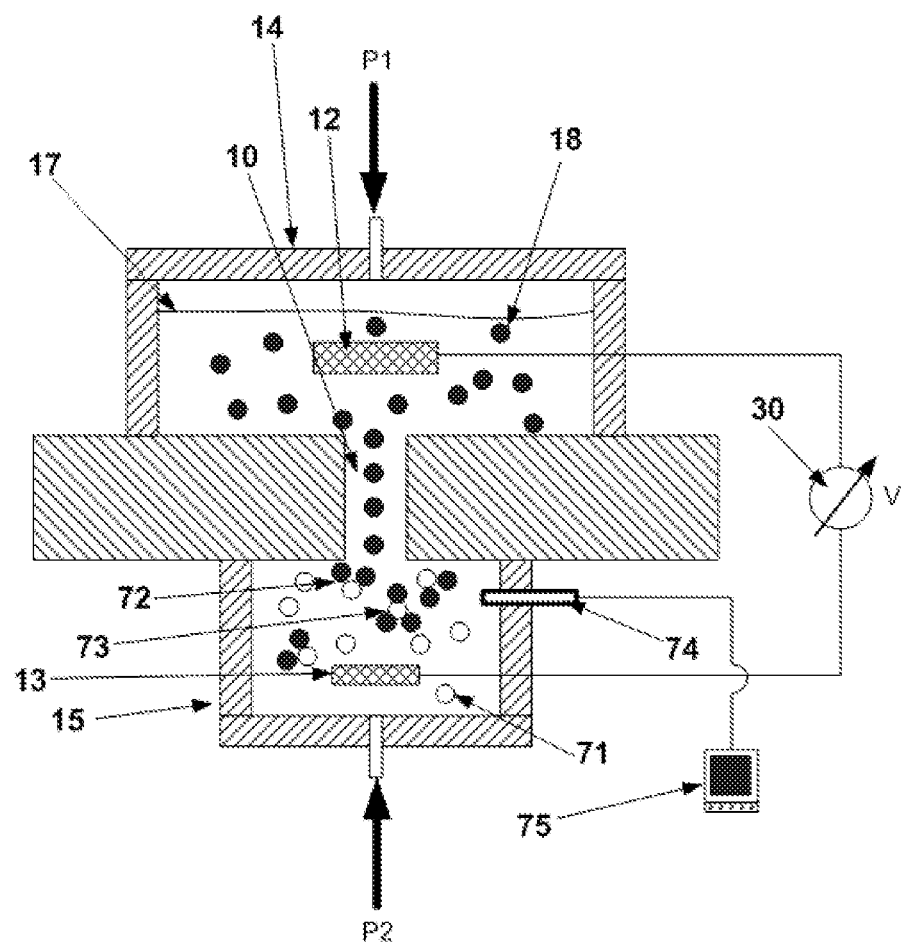
FIG. 7 diagrammatically illustrates the use of an electrophoresis system in another possible application of the invention showing the ability of the system to measure and control reactions.

Another application of the invention is to enable the delivery of measured quantities of particles to a reaction. Referring to FIG. 7, movement of the particles 18 in the fluid 17 through the aperture 10 is controlled by a combination of the pressure differential (P1-P2) and the potential 30 across the electrodes 12 and 13, as described above. In this manner the particles 18 are delivered to the reservoir 15 that already contains particles 71. When the particles 71 come into contact with the particles 18 a reaction takes place so as to create particles 72. Each particle 72 is the result of a specific reaction between two particles 18 and one particle 71. As will be known to those skilled to the art, the rate of the reaction that creates the particles 72 can be controlled by the rate of delivery of the particles 18 into the fluid 17 containing the particles 71. It will be appreciated that in this manner it is possible to control of the reactions by delivering measured amounts of one type of particle to a solution containing another type of particle.

Reversal of the pressure and/or voltage can be used to enable the particles to be analysed and/or their size and/or charge to be extracted.

Another application of the invention is to enable the real time observation of particles and particle formation. Referring to FIG. 7, a measuring probe 74 is inserted though the wall of the reservoir 15 to enable the real time observation of particles. The measuring that can be implemented by such a probe 74 include, but are not limited to, fluorescence spectroscopy, mass spectroscopy, X-ray spectroscopy, atomic absorption spectroscopy, infrared spectroscopy, near infrared spectroscopy, Raman spectroscopy, static laser scattering, dynamic light scattering, phase analysis light scattering, nanoparticle tracking analysis and surface plasmon resonance.

Regardless of the measurement technique used, information concerning the reaction is delivered by the measuring probe 74 to a measuring device 75 that interprets the measurement and stores data relevant to the measurement. For instance, if a particle 72 will, under certain conditions, take on another particle 18 and become particle 73, the detection and measurement technique applied through the probe 74 will be able to detect and report this formation to the user. Thus it is possible to provide measurement data that characterizes changes in the particles over time. It is also possible to observe and measure Brownian motion of the particles 71, 72 and 73 within the fluid 17 through the probe 74 by means described.

In one possible application of the invention, the particle 18 in FIG. 7 may be an antibody that is delivered in measured quantities to a collection of viruses 71 in blood. The probe 74 will then be able to measure the effect of the antibody on the viruses 71.

As described above, one implementation of the invention has the ability to determine the quantity of particles that travel through an aperture over time. This enables a user to determine the concentration of particles in solution by measuring the quantity of particles that travel though an aperture over a period of time. If the flow rate of the solution is known, the concentration of particles in solution can be calculated by dividing the quantity of particles that has flowed though the aperture by the volume of fluid that flowed though the aperture over a certain period of time. Where the flow rate of solution is unknown, the concentration of particles can be calculated using calibration particles of known concentration.

In a further application of the invention the user is provided with the ability to deliver a measured amount of solution flow over a period of time though an aperture. Referring to FIG. 1, the number of particles 18 that flow through the aperture 10 over a period of time, or the rate of particle flow, is determined by the following parameters:
1) The pressure differential P1-P2 between the reservoirs 14 and 15.
2) The potential difference across the electrodes 12 and 13.
3) The concentration of particles 18 in the fluid 17.
4) The type or polarity of particles 18 in solution.
5) The hole size of the aperture 10.

Figure 8:
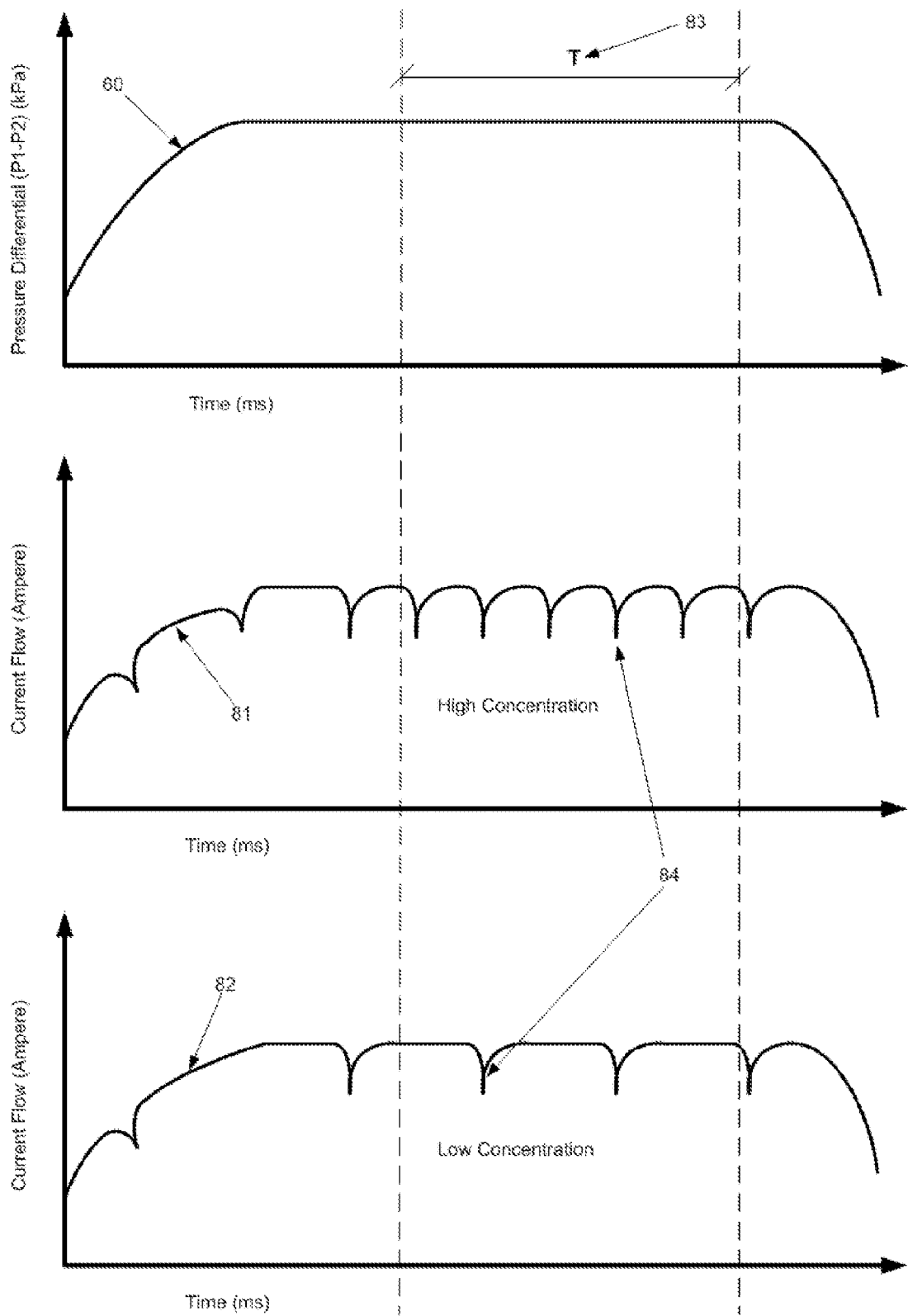
FIG. 8 are graphs of pressure differential (P1-P2) against time and current against time, showing a pressure trace and current traces for different concentrations, illustrating the ability of the invention to determine the concentration of particles in solution.

Referring to FIG. 8, it follows and will be apparent to those skilled in the art that if the listed parameters are kept constant in the system, the current data trace should detect the same quantity of events 84 of particles travelling through the aperture 10 over a certain period of time. A representative pressure differential 80 and current trace 81 versus time is shown in FIG. 8 for a known concentration of particles in solution. As the pressure differential 80 ramps up to a steady state, the events in the current trace 81 become periodic and stable. Thus, over the time window 83 shown, if the concentration of particles is known, the flow rate of the solution can be calculated by counting the number of particles flowing through the aperture 10 (number of events in the trace 81). The number of particles is divided by the concentration of particles in the solution to determine the amount of flow for the pressure differential 80 during the time window 83. The flow rate is determined by dividing the amount of flow by the period of the time window 83.

If the same pressure profile is applied to an unknown concentration in the same solution, the system will be able to determine this concentration by counting the number of events in the current trace 82. Since the flow rate was already calibrated by the trace 81, the new concentration can be determined by dividing the number of events by the flow rate.

In a similar fashion, it is also possible to calculate the total quantity of fluid that was transferred from one reservoir to another for the total duration of a pressure pulse, such as the pressure differential 80 in FIG. 8. By counting the number of particles of known concentration that flow through the aperture during the total duration of the pressure pulse, the quantity of fluid transferred can be determined. If the same pressure pulse is then applied to a new, unknown particle concentration in the same solution, the particle concentration of that solution can be determined by counting the number of events or particles for that concentration.

It is further possible to enable a user to determine the particle concentration in a solution of particles that are different from the particles used to calibrate the system. When different particles are used, the duration and amplitude of the events in the current trace will be different to those used for calibration. However, one event is generated per particle that flows through the aperture 10 and therefore, regardless of the magnitude of the event, the presence of a particle will be accounted for by such an event. Therefore the number of particles that has travelled though the aperture can be determined and the particle concentration can thus be calculated.

The methods described above can normally only be applied if the translocation rate of particles due to pressure is significantly higher than the translocation rate due to electrophoresis. However it is possible to introduce a correction factor and account for the translocation frequency due to electrophoresis where this is significant relative to the translocation rate due to pressure.

Figure 9:
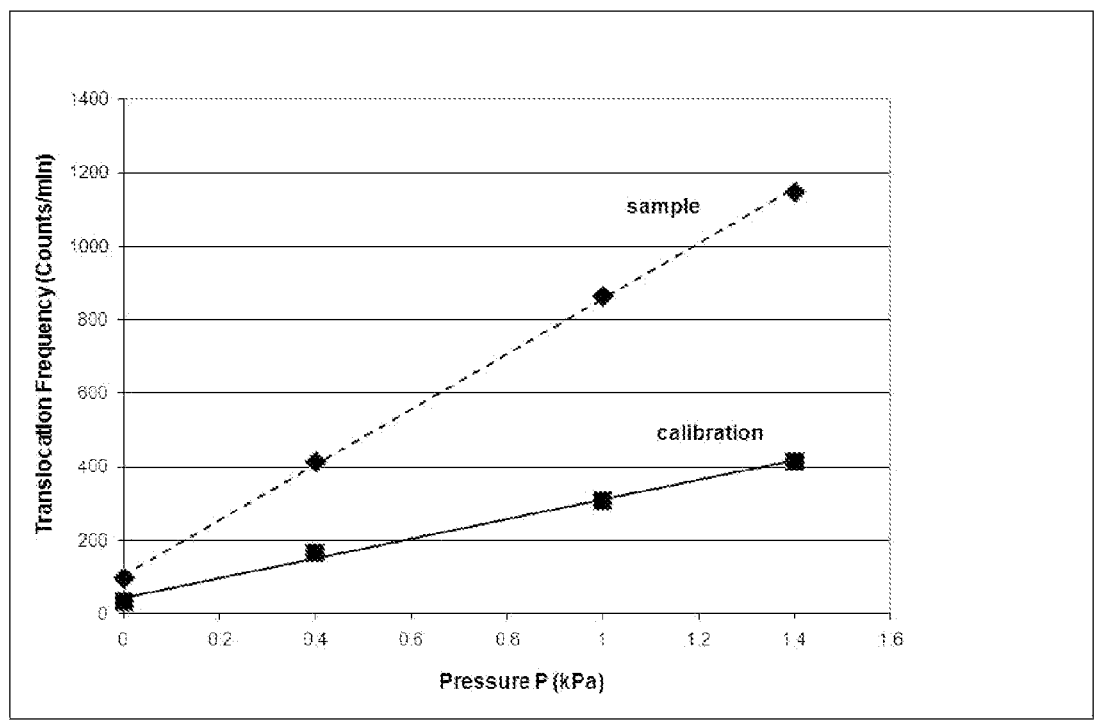
FIG. 9 illustrates the use of pressure to calculate the concentration of particles, using calibration particles of know concentration.

It is also possible to enable the user to determine the particle concentration in a solution of particles that are different from the particles used to calibrate the system. In this case the method is based on measuring the rate of translocation across the aperture of calibration particles for at least two different pressures, one preferably P=0. Then the same measurement is repeated for a sample of particles of unknown concentration. The rate of translocation versus pressure can then be plotted as a linear relationship. The unknown concentration can then be calculated from the slopes of the linear relationships. This is possible because the slopes of the fitted lines are proportional to the pertinent concentrations of particles. An example illustrating this method is shown in FIG. 9. This method for calculating the concentration of an unknown sample takes account of both the translocation rate due to electrophoresis and the translocation rate due to pressure, and hence is more general than the method described previously.

Another application of the invention allows for the characterization of the hole size of the aperture 10 (FIG. 1). As described above, a certain type of particle 18 in a specific solution 17 with a certain pressure differential (P1-P2) and potential 30 over electrodes 12 and 13 will induce a certain amount of events 84 over a defined time period 83 for a given aperture size. If the aperture size is increased, the flow rate through the aperture 10 will increase and therefore cause more events 84 to be observed in the system. Thus, by correlating certain event rates with specific aperture hole sizes under particular operating conditions, an unknown size of aperture can be identified by the number of events under pre-set conditions.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein. For example, the features of any of the claims may be combined with the features of any other claim.

The invention claimed is:

1. A method of controlling the flow of particles in or through an aperture between two reservoirs, the method comprising suspending the particles in a fluid within the aperture, applying a potential difference across the aperture so as to tend to electrophoretically transport the particles between a region of higher potential and a region of lower potential in the fluid to produce an output current, applying a pressure differential across the aperture so as to tend to transfer the fluid with the particles therein through the aperture from a high-pressure reservoir to a low-pressure reservoir, monitoring the particles before and/or during and/or after passage through the aperture by measuring the output current, and adjusting the potential difference and/or the pressure differential across the aperture in order to achieve control over the translation and in order to achieve control over the measurement of the particles within the aperture, wherein the concentration of the particles in the fluid is determined in dependence on the potential difference and/or the pressure differential applied across the aperture, and wherein the concentration of the particles in the fluid is determined by monitoring (i) the quantity of particles that pass through the aperture under different pressure conditions, and (ii) the quantity of particles in a fluid of known particle concentration that pass through the aperture under different pressure conditions.

2. A method according to claim 1, wherein the potential difference and/or the pressure differential across the aperture is adjusted during translation of the particles through the aperture to control the velocity of the particles.

3. A method according to claim 1, wherein the potential difference and/or the pressure differential across the aperture is adjusted to control the delivery through the aperture of an exact required quantity of particles to one of the reservoirs.

4. A method according to claim 1, wherein the velocity of the particles is determined in dependence on the potential difference and/or the pressure differential applied across the aperture.

5. A method according to claim 1, wherein the charge and/or zeta-potential of the particles is determined in dependence on the potential difference and/or the pressure differential applied across the aperture.

6. A method according to claim 1, wherein the particle size of the particles is determined in dependence on the potential difference and/or the pressure differential applied across the aperture.

7. A method according to claim 1, wherein the concentration of the particles in the fluid is determined by monitoring the quantity of particles that pass through the aperture in a particular time period.

8. A method according to claim 1, wherein the particles in the fluid are pre-calibrated, and the size of the aperture is determined according to the effect of the potential difference and/or the pressure differential applied across the aperture on the pre-calibrated particles.

9. A method according to claim 1, wherein the particles in the fluid are of different types, and the identity of at least one type of particles is determined according to the effect of the potential difference and/or the pressure differential applied across the aperture as the particles flow through the aperture.

10. A method according to claim 1, wherein the particles in the fluid are of different charges, and the particles of different charges are separated from one another in dependence on the different effects of the potential difference and/or the pressure differential applied across the aperture on the particles.

11. A method according to claim 1, wherein the particles are monitored by a monitoring probe which provides an output indicative of the position of at least one of the particles with respect to time, the monitoring probe preferably utilizing one of fluorescence microscopy, nanoparticle tracking analysis, other microscopy based imaging, phase analysis light scattering, and near infrared chemical imaging.

12. A method according to claim 1, wherein a degree of aggregation of the particles is determined in dependence on the potential difference and/or the pressure differential applied across the aperture.

13. A method according to claim 1, wherein the particles are monitored by a monitoring probe that provides an output indicative of the particles detected, the monitoring probe preferably utilizing one of fluorescence spectroscopy, mass spectroscopy, X-ray spectroscopy, atomic absorption spectroscopy, infrared spectroscopy, near infrared spectroscopy, Raman spectroscopy, static laser scattering, dynamic light scattering, phase analysis light scattering, nanoparticle tracking analysis and surface plasmon resonance.

* * * * *